United States Patent [19]

Shaw

[11] Patent Number: 4,569,238

[45] Date of Patent: Feb. 11, 1986

[54] MULTI-LAYER LIQUID SAMPLER

[76] Inventor: Merle C. Shaw, P.O. Box 1340, Phelan, Calif. 92371

[21] Appl. No.: 714,907

[22] Filed: Mar. 22, 1985

[51] Int. Cl.$^4$ .............................................. G01N 1/12
[52] U.S. Cl. .................................................. 73/864.65
[58] Field of Search ........... 73/864.63, 864.65, 864.66, 73/864.67; 33/126.4 R

[56] References Cited

U.S. PATENT DOCUMENTS

| | | | |
|---|---|---|---|
| 2,580,711 | 1/1952 | Weidinger | 73/864.65 |
| 2,634,612 | 4/1953 | Quist | 73/864.63 |
| 4,346,519 | 8/1982 | Milo | 73/864.63 |

Primary Examiner—S. Clement Swisher
Attorney, Agent, or Firm—Edward E. Roberts

[57] ABSTRACT

A multi-layer liquid sampler in which one side of the length of a non-sparking plate is fastened to a submersing rod. The other side is fastened to top and bottom of tube holders that contain a transparent glass or plastic tube. That tube is kept in a prepositioned attitude in relationship to the tube by means of a plastic positioner ring with circular openings for the tube and two legs of a non-sparking metal rod that is bent into a "U" shape. The bottom of the "U" is bent forward and flattened slightly to become the ledge of a closure. The other piece of the closure is a beryllium copper spring that is fastened at one end in close relationship with the bottom holder and non-sparking plate. A number of non-sparking metal screwheads and nuts are on the bottom and a plastic cone fastened to the spring and located under the transparent tube. This cone seals the bottom of the tube by contact between the tube and cone about two-thirds of the distance down the cone. A string attaches to the end of the spring allowing samples to be taken at any depth in the tank or storage container. One of the non-sparking metal screws on the bottom of the beryllium copper spring is a touching screw that has the purpose of touching the bottom first and closing the spring onto the flattened forward bending "U" of the rod when a string is not used for closure. This sampler enters the storage tank in an open position and thus allows any liquids which have layered to pass through the sampler and be trapped. This could not be achieved if the sampler only opened and closed upon contact with the bottom of the tank if there were more than two layers present.

9 Claims, 5 Drawing Figures

MULTI-LAYER LIQUID SAMPLER

BACKGROUND OF THE INVENTION

Field of the Invention

This invention relates to the field of liquid sampling in general and to sampling specified strata of liquids in a storage means in particular.

SUMMARY OF THE INVENTION

In the field of liquid samplers it has become more and more a requirement of the industry that one be able to sample the liquid being tested, at various levels. This is done in order to fully test the liquid and determine its characteristics at any level. Many liquids are known to layer and thus give false readings as to the volume of various components of these layers. For instance, in gasohol storage component separation can occur. This can result in a bottom layer of sludge, an intermediate layer of water or water-alcohol mixture and a top layer of gasoline. One would sample the gasoline layer alone and determine its limits if one was interested in the quantity of gasoline available alone. This, however, would not take into account the two other layers and would be just approximately correct. One would sample the sludge layer and determine its limits if one was interested in the products that form or wanted to determine if the tank needed cleaning or was interested in the volume of sludge present. The water or water-alcohol layer might be sampled to determine the amount present. This determination would allow the necessary cleaning, pumping, mixing or alcohol addition to be made.

The creator of this invention has watched persons test liquid storage volumes for contents with solid sticks or rods. He has noted them testing liquid volumes with open bottles, beakers or samplers that only open and close at the bottom of the tank. He has seen that their present procedures are faulty and fail to give a true reading of the volumes tested. The present invention has been the result of his research.

A hollow glass tube about 1.5 cm in diameter is mounted on the top and bottom of a brass mounting bracket. A brass rod is bent to form a "U". The two legs are formed into two brass protective rods which help hold the mounting brackets in place. They themselves are held in position by a rod positioner on the bottom and the top mounting bracket. In their parallel position opposite each other, they help guard the glass tube from breakage. A beryllium copper closure spring plate is mounted on one side of the bottom bracket opposite the protective rods. This plate is normally in the open position. Directly below the bottom opening of the glass tube is mounted a plastic cone, small side up on the beryllium copper closure plate. The bottom diameter of the cone forms a close fit with the glass tube effectively sealing such glass tube a small distance up the cone when the spring is latched shut. The latch is formed of the bottom of the "U" rod. The "U" which is bent forward and flattened so that the bottom of the protective rods interacts to form an interference fit with the inwardly bent free position of the beryllium closure spring. The closure spring is normally braced open. As the liquid sampler descends into the various layers liquids pass slowly through the glass tube until the sampler reaches bottom. The beryllium copper spring is so constructed that it will close and engage the latch when the weight of the multi-phase bottom sampler rests upon it.

The free end of the beryllium copper spring is bent upward for fastening a string or wire trip after being bent inward to accommodate the latch. This end is punched with a small hole to which the string or wire is attached enabling one to take samples at any level of the liquid being tested.

It is an object then of this invention to provide a liquid sampler that would immediately inform the person sampling the liquid if various layers of other liquids are present in the sampled liquid.

It is another object of this invention to provide a liquid tester that will enable a person sampling the stored liquid to determine the approximate amount of each layer that has formed within the sampled liquid.

These and other objects of the invention will become apparent from the drawing and the description of the preferred embodiment that follows.

DESCRIPTION OF THE PREFERRED EMBODIMENT

Figure 1:
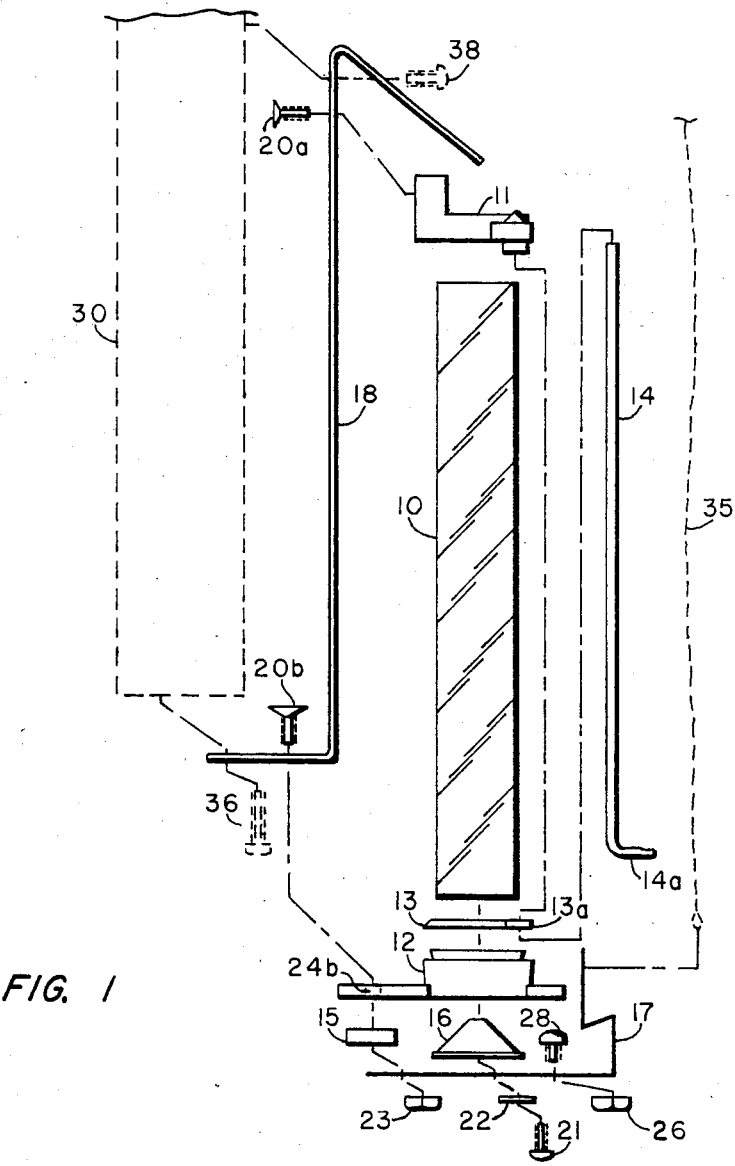
FIG. 1 is an exploded side view of the invention.

In FIG. 1 the invention is clearly seen as all of its components are shown in an exploded view. 10 is a threaded transparent glass tube open at both ends that is the testing viewer of the invention. Glass tube and support holders are located at the top 11 and bottom 12. A plastic positioner 13 fits around the tube and each leg of the brass protective rod 14 that is bent into a "U"-shape. The bottom of the "U" 14a is bent outward and flattened to form a ledge upon which the bent portion of 17, the beryllium copper closure spring, catches to close tube 10 at the bottom. The actual closure is done by a soft plastic cone 16 that comes in contact with the bottom of tube 10 about two-thirds of the way down the cone 16 giving a force seal when the spring 17 in the closed and locked position. The spring 17 is normally under slight tension in the open position. The open position is about 1 mm in the direction away from the tube 10. This permits liquid to flow slowly from the bottom into the tube 10 past cone 16. All the parts are held together by a brass support plate 18. This plate 18 engages top tube support 11 and is held in place by screw 20a. Bottom plastic tube support 12 is held in place against brass plate 18 by screw 20b which passes through a hole in the plastic 24b through plastic spacer 15 through hole 29 in the beryllium copper spring and is fastened in place by nut 23. The entire assembly is held tightly in place. Positioner plastic ring 13 holds the two rod legs 14 in two round holders 13a and encircles tube 10 thus holding three parts, tube 10, brass rod 14 and 13 in a preplaned relationship. The tube 10 is closed at the bottom by means of a soft plastic cone 16 which is fastened to beryllium copper closure spring 17 by means of screw 21. A prethreaded hole is placed in the center bottom of plastic cone 16. A touching screw 28 is added with a nut 27. The purpose is to have screw 28 touch the bottom first and force spring 17 to the closed position whenever string 35 is not used for the same purpose. String 35 is designed to enable the contents of the tank or holding container to be sampled at any level by closing spring 17 which is bent upward and has a small hole 39 punched in it to accommodate the string.

The testing device is normally used by attaching wooden or metal rod 30 to the liquid sampler by means of screw 36 through either hole 25a, 25b or 25c, to the end of rod 30. Screw 38 is passed through hole 41 into the side of rod 30 which helps give rod 30 and the liquid sampler tube 10 greater stability in relation to each other. All metal parts are brass or some other non-sparking metal for absolute safety in petroleum product sampling.

Figure 2:
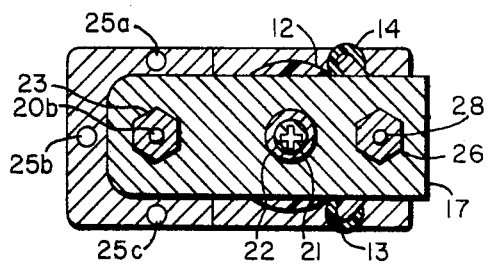
FIG. 2 is a bottom view of the invention.

In FIG. 2 can be seen the bottom of the liquid sampler. Note that the beryllium copper spring 17 and brass bracket 18 can be seen in great detail. The screw 21 holding the cone 16 to spring 17 can be seen in place. Nut 23 can be seen in place holding spring 17, plastic part 12 and spacer 15 (shown only in FIG. 1), in a tight combination by being tightened onto screw 20b. First bottom touching screw 28 can also be seen in place on spring 17.

Figure 3:
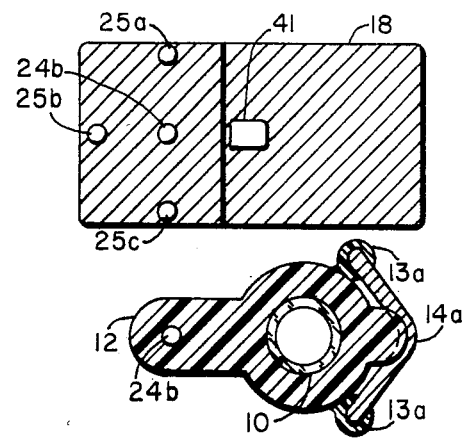
FIG. 3 is a bottom view of the brass support plate and plastic tube holder.

In FIG. 3 can be seen a bottom view with the spring 17 (not shown) and the brass plate 18 set above. The screwholes to contain screws 20b and 36 can be seen as well as slot 41 which enables one to fasten screw 38 through brass bracket 18 into rod 30. The bottom of plastic part 12 can also be seen. Threaded tube 10 extends completely through part 12 and the bending forward of rod 14 at 14a can clearly be seen. This rests upon a forward projection of piece 12. The way rod 14 is passed through the center of the projections from plastic piece 13 which holds them in spaced relationship with tube 10 can also be seen.

Figure 4:
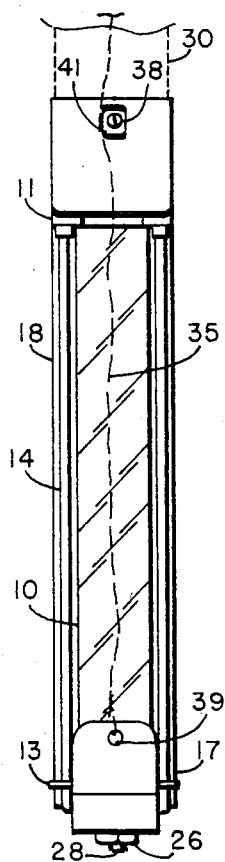
FIG. 4 is a front view of the invention.

FIG. 4 is a front view of the invention. The slot 41 can be clearly seen giving access to the screwhead of screw 38. String 35 and rod 30 are also shown in place. The glass tube 10 is shown going up into top plastic support holder 11. Note that rod legs 14 insert into holes in top plastic support holder 11. By cooperation with plastic spacer 13 the rods are kept in parallel relationship with glass tube 10. The bent position of spring 17 can also be seen which forms a catch on part 14 and a hole 39 for insertion of string 35.

Figure 5:
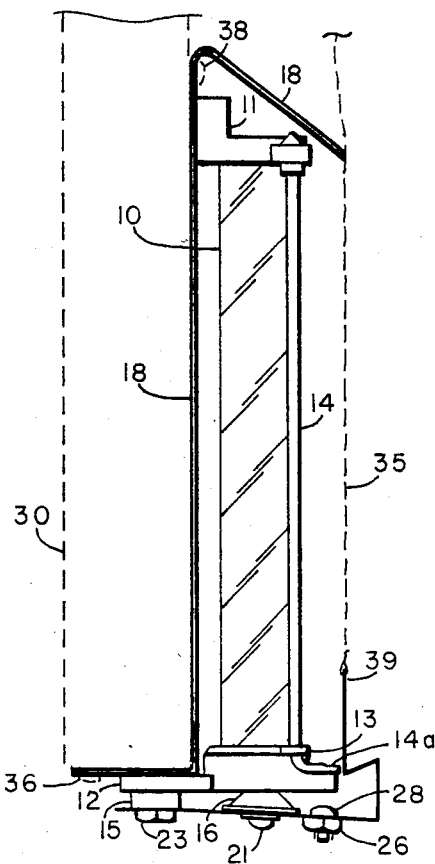
FIG. 5 is a side view of the invention.

In FIG. 5 is seen a side view of the liquid sampler. Viewing tube 10 can be seen extending into top plastic holder 11 through plastic spacer 13 and label with the bottom of plastic holder 12. Cone 16 is seen in place on spring 17. The cooperation of pieces 12, 15 and 17 of the device can be clearly seen. The screws, washers and nuts and their relationships with the parts are clearly shown. In mode of action the liquid tester is first attached to rod 30. Spring 17 is in the normal open position. The rod and tester are slowly inserted into an underground petroleum products or water tank. Fluid enters the tester past cone 16 and through the top of tube 10 even with plastic part 11 when the tester is submerged in the liquid. As the tester passes through different layers the fluid passes into the bottom and out the top. When the bottom is reached screw 28 touches first and forces spring 17 into the closed position. The tester is withdrawn showing the composition of the bottom layer of the tank. A string 35 may be added to determine the composition of the layer at any depth.

It is obvious to one skilled in the art that many variations of this invention can be developed. All however are within the spirit and scope of the attached claims.

I claim in combination;

1. a multi-layer liquid sampler composed of;
a support plate means;
attached to upper and lower tube holder means;
a hollow transparent tube means passing through both holders;
a one piece rod means;
the rod means is bent or designed to have a forward bent "U" shape on the bottom and two equal legs;
a plastic positioning piece designed to hold the tube means a fixed distance from the rod means;
a beryllium copper thin metal spring;
the end third of the spring is bent upward about 1 cm inward and downward about 0.5 cm and then upward about 2 cm;
a plastic cone is mounted on the upper end of the spring and extends into the glass tube;
appropriate non-sparking screws, washers and nuts hold the spring, a spacer and bottom holder to the support plate; and,
a first bottom non-sparking metal touching screw attached to the bottom of the metal spring.

2. A multi-layer liquid sampler like in claim 1 in which the support plate means is a non-sparking metal.

3. A multi-layer liquid sampler like in claim 1 in which the support plate means is a plastic material.

4. A multi-layer liquid sampler like in claim 1 in which the upper or lower tube holder means are plastic.

5. A multi-layer liquid sampler like in claim 1 in which the upper and lower tube holder means are a non-sparking metal.

6. A multi-layer liquid sampler like in claim 1 in which the hollow tube means is glass.

7. A multi-layer liquid sampler like in claim 1 in which the hollow tube means is transparent plastic.

8. A multi-layer liquid sampler like in claim 1 in which the one piece rod means is a non-sparking metal.

9. A multi-layer liquid sampler like in claim 1 in which the one piece rod means is plastic molded to the finished form.

* * * * *